United States Patent [19]
Atkinson

[11] 4,189,602
[45] Feb. 19, 1980

[54] ACID OXIDATION PROCESS

[75] Inventor: John H. Atkinson, Middlesbrough, England

[73] Assignee: Imperial Chemical Industries Limited, London, England

[21] Appl. No.: 902,108

[22] Filed: May 2, 1978

[30] Foreign Application Priority Data

May 13, 1977 [GB] United Kingdom ............... 20240/77

[51] Int. Cl.² ............................................. C07C 39/06
[52] U.S. Cl. .................................................... 568/801
[58] Field of Search ................................ 568/801, 800

[56] References Cited

U.S. PATENT DOCUMENTS

| Re. 24848 | 7/1960 | Kaeding et al. | 568/801 |
|---|---|---|---|
| 2,727,926 | 12/1955 | Kaeding et al. | 568/801 |
| 2,852,567 | 9/1958 | Barnard et al. | 568/801 |
| 3,277,184 | 10/1966 | Ryland et al. | 568/801 |

Primary Examiner—Werren B. Lone
Attorney, Agent, or Firm—Cushman, Darby & Cushman

[57] ABSTRACT

In the copper catalysed oxidation of p-toluic acid to meta-cresol at an elevated temperature the problem of acid sublimation is avoided by oxidizing the para-toluic acid in admixture with benzoic acid.

2 Claims, No Drawings

ACID OXIDATION PROCESS

The present invention relates to the oxidation of a benzoic acid to a phenol in particular to the oxidations of para-toluic acid to meta-cresol.

A method of manufacturing phenol is described in U.S. Pat. No. 2,727,926 and consists in oxidising benzoic acid in the liquid phase at a temperature in excess of 200° C. in the presence of a copper compound catalyst. The copper compound must be soluble in the reaction medium and is therefore preferably an organic salt, particularly cupric benzoate. The catalyst may also be promoted by the addition of other metals, e.g. magnesium, sodium, potassium, lithium, cobalt or barium in the form of their salts, oxides or hydroxides. For the reaction to be continuous oxygen is necessary, either as gaseous oxygen or, more conveniently, in the form of air. The overall process also requires the presence of steam to obtain significant yields of phenol.

It has been suggested that this manufacturing process for phenol may also be applied to analogues of benzoic acid provided that the analogue does not contain a substituent which affects, or is affected by the oxidation process. Analogues which have been proposed as being suitable include the toluic acids, nitro-benzoic acids, chlorobenzoic acids, methoxybenzoic acids, p-phenylbenzoic acid and 2,4-dimethylbenzoic acid. Any of these analogues, it has been suggested, may be used in the process simply by replacing the benzoic acid by the acid in question. It has been our experience however that when para-toluic acid is the reactant acid and thus forms the liquid phase of the reaction medium considerable operating difficulties arise due to sublimation of the acid with ensuing blockage of pipelines and plant vessels. We have now surprisingly found that this operating difficulty may be resolved by oxidising the para-toluic acid in admixture with benzoic acid.

According to the invention therefore a process for the oxidation of para-toluic acid to meta-cresol comprises contacting a liquid phase comprising a mixture of para-toluic acid and benzoic acid with oxygen and steam at an elevated temperature in the presence of a copper compound which is soluble in the reaction medium.

The product of the oxidation process is a mixture of meta-cresol and phenol which is conveniently continuously distilled out of the reaction mixture as the oxidation proceeds. For certain purposes the mixture of phenol and meta-cresol may be used directly but more often the two are separated, preferably by distillation. If desired the phenol and meta-cresol may be separated by leading the gases leaving the oxidation process through a fractional distillation zone where the 20° C. difference in boiling point between phenol and meta-cresol enables an easy separation to be made. It is one of the advantages of the process that it can provide a supply of meta-cresol which is purer than that usually available commercially.

As the prime product of the process is meta-cresol it is preferred to maintain the amount of benzoic acid in the reaction medium at a minimum. Although therefore the weight ratio of benzoic acid to para-toluic acid may be as high as 3:1 of even 6:1 it is preferably in the range 1:3 to 1:1.

The oxidation process takes place at an elevated temperature, generally greater than 200° C. but significantly below the boiling point of benzoic acid (249° C.). Preferably the temperature is in the range 205° to 230° C.

The copper compound catalyst must be soluble in the reaction medium but may be added in a variety of forms, e.g. as an inorganic or organic salt (for example cupric acetate) or as oxide or hydroxide or even as the metal because in the reaction medium the copper dissolves as a salt of benzoic and/or para-toluic acid. For the sake of convenience and to avoid introducing extraneous anions into the reaction medium the copper is preferably added as cupric oxide, cupric benzoate or cupric para-toluate. The concentration of copper in the reaction medium is preferably 0.5 to 10% by weight of the combined benzoic and para-toluic acids, more preferably 1 to 5% by weight.

The oxidation reaction may if desired be enhanced by the addition of a promoter which may be chosen from those listed earlier in this specification. The preferred promoters are cobalt and magnesium, particularly the latter, and although they may be added as any compound which is soluble in the reaction medium, for example as an inorganic or organic salt, oxide or hydroxide, the oxide, benzoate or para-toluate are preferred. The promoter may be used in a concentration from 0.5 to 15% by weight of the combined benzoic and para-toluic acids, preferably 1 to 7% by weight.

The oxygen which is used in the oxidation reaction is preferably supplied in the form of air. It is also necessary for steam to be present in the reaction medium, the steam being fed together with the air or oxygen or as a separate gas flow. The amounts of steam and oxygen supplied to the reaction medium are not critical provided that the latter is supplied in an amount in excess of the stoichiometric amount required for the reaction. In general however the greater the flow of steam the better.

The reaction is, for reasons of convenience, preferably carried out at atmospheric pressure. Elevated or reduced pressures may be used if desired and in such cases the temperature of oxidation may need adjustment to take into account the change in boiling point of the phenol and meta-cresol produced. The reaction may be carried out batchwise but is particularly suited to continuous or semicontinuous operation.

The invention will now be further described by means of the following Examples. The oxidation apparatus used in each case consisted of a 500 ml. flanged oxidation flask provided with a cruciform stirrer and a fractionation column (a lagged 7-plate 1-inch Oldershaw column). Steam was raised by pumping water through an electrically heated, ceramic bead-filled, metal tube and was mixed with preheated air and passed through the stirrer into the flask. The contents of the flask were heated by infra-red lamps in the case of Example 1 and by means of an electric mantle in Examples 2 to 7.

At the start of each experiment, the solid acids were mixed, in the amounts indicated, with copper compound and promoter compound and heated with stirring until molten. A period of time was allowed for the metals to be converted as necessary to the form of the organic salts before the temperature was raised to the reaction temperature and the air and steam introduced. The vapours leaving the flask passed through the fractionation column, allowing the phenol, meta-cresol, water and some aromatic acid to be collected in a receiver. The distillate was made homogeneous by the addition of an appropriate known weight of isopropanol and the phenol and meta-cresol content determined by gas-liquid chromatography.

EXAMPLE 1

| Initial charge of reactants: | Benzoic Acid | 100 g. |
| --- | --- | --- |
| | Para-toluic Acid | 100 g. |
| | Cupric Oxide | 4.6 g. |
| | Magnesium Oxide | 7.0 g. |
| Steam flow rate | 150 g/hour | |
| Air flow rate | 30 liters/hour | |
| Reaction temperature | 210°-200° C. | |

After 18 hours, the conversion of para-toluic acid was 81% and the yield of meta-cresol (based on para-toluic acid converted) was 51%.

EXAMPLE 2

| Initial charge of reactants: | Benzoic Acid | 125 g. |
| --- | --- | --- |
| | Para-toluic Acid | 125 g. |
| | Cupric Acetate | 28.9 g. |
| | Magnesium Oxide | 17.5 g. |
| Steam flow rate | 100–150 g./hour | |
| Air flow rate | 30–60 liters/hour | |
| Reaction temperature | 230° C. | |

After 14 hours, 53% of the para-toluic acid had been converted and the yield of meta-cresol was 42.2%.

EXAMPLE 3

| Initial charge of reactants: | Benzoic Acid | 125 g. |
| --- | --- | --- |
| | Para-toluic Acid | 125 g. |
| | Cupric Acetate | 28.9 g. |
| | Magnesium Oxide | 17.5 g. |
| Steam flow rate | 100 g./hour | |
| Reaction temperature | 230° C. | |

Air and nitrogen were passed alternately through the reaction mixture throughout the reaction, air for 5 minutes at a flow rate of 60 liters/hour alternating with nitrogen for 10 minutes at a flow rate of 30 liters/hour. After 12 hours, 33.4% of the para-toluic acid had been converted and the yield of meta-cresol was 59.6 percent.

EXAMPLE 4

| Initial charge of reactants: | Benzoic Acid | 125 g. |
| --- | --- | --- |
| | Para-toluic Acid | 125 g. |
| | Cupric Acetate | 14.4 g. |
| | Magnesium Oxide | 8.75 g. |
| Steam flow rate | 75 g./hour | |
| Air flow rate | 30 liters/hour | |
| Reaction temperature | 230° C. | |

After 16 hours, the conversion of para-toluic acid 10 was 44.5 percent and the yield of meta-cresol was 38.1 percent.

EXAMPLE 5

| Initial charge of reactants: | Benzoic Acid | 220 g. |
| --- | --- | --- |
| | Para-toluic Acid | 220 g. |
| | Cupric Oxide | 11.4 g. |
| | Magnesium Oxide | 18.8 g. |
| Steam flow rate | 160 g./hour | |
| Air flow rate | 30 liters/hour | |
| Reaction temperature | 230° C. | |

After 8 hours, the conversion of para-toluic acid was 42.8 percent and the yield of meta-cresol was 44.7 percent.

EXAMPLE 6

| Initial charge of reactants: | Benzoic Acid | 110 g. |
| --- | --- | --- |
| | Para-toluic Acid | 110 g. |
| | Cupric Oxide | 5.7 g. |
| | Magnesium Oxide | 9.4 g. |
| Steam flow rate | 130 g./hour | |
| Air flow rate | 30 liters/hour | |
| Reaction temperature | 230° C. | |

After 2.5 hours, and at 2.5-hour intervals thereafter, further charges of 10 g. of benzoic acid and 10 g. of para-toluic acid were added unitl the total additional weight of each acid amounted to 80 g. (making 190 g. total weight of each acid). At the end of 23 hours from the start of the reaction, 59.4 percent of the total weight of para-toluic acid had been converted and the yield of meta-cresol amounted to 47.2 percent, based on the weight of para-toluic acid converted.

EXAMPLE 7

| Initial charge of reactants: | Benzoic Acid | 110 g. |
| --- | --- | --- |
| | Para-toluic Acid | 110 g. |
| | Cupric Oxide | 5.7 g. |
| | Magnesium Oxide | 9.4 g. |
| Steam flow rate | 130 g./hour | |
| Reaction temperature | 230° C. | |

Air and nitrogen were passed alternately through the reaction mixture throughout the reaction, air for 5 minutes at a flow rate of 60 liters/hour alternating with nitrogen for 10 minutes at a flow rate of 30 liters/hours. After 2.5 hours, and at 2.5-hour intervals thereafter, further charges of 10 g. of benzoic acid and 10 g. of para-toluic acid were added until the total additional weight of each acid amounted to 70 g. (making 180 g. total weight of each acid). At the end of 25 hours from the start of the reaction, 60.7 percent of the total weight of para-toluic acid had been converted and the yield of meta-cresol amounted to 52.6 percent, based on the weight of para-toluic acid converted.

I claim:

1. A process for the oxidation of para-toluic acid to a product containing meta-cresol comprising contacting a liquid phase containing para-toluic acid and benzoic acid in a weight ratio of 3:1 to 1:3, with oxygen and steam at a temperature greater than 200° C. and significantly below 249° C. and in the presence of a copper compound catalyst selected from the group consisting of cupric oxide, cupric benzoate, cupric para-toluate and cupric acetate, wherein the quantity of copper compound is such that the concentration of copper in the reaction medium is 0.5 to 10% by weight of the combined weight of benzoic acid and para-toluic acid.

2. A process for the oxidation of para-toluic acid to a product containing meta-cresol comprising contacting a liquid phase containing para-toluic acid and benzoic acid with oxygen and steam at a temperature greater than 200° C. and significantly below 249° C. and in the presence of a copper compound catalyst selected from the group consisting of cupric oxide, cupric benzoate and cupric para-toluate, wherein the quantity of copper compound is such that the concentration of copper in the reaction medium is 0.5 to 10% by weight of the combined weight of benzoic acid and para-toluic acid.

* * * * *